United States Patent [19]
Aurelian et al.

[11] Patent Number: 5,919,616
[45] Date of Patent: Jul. 6, 1999

[54] SEROLOGICAL ASSAY FOR HERPES

[75] Inventors: Laure Aurelian, Baltimore; Gary J. Calton, Elkridge, both of Md.

[73] Assignee: AuRx, Inc., Elkridge, Md.

[21] Appl. No.: 08/989,291

[22] Filed: Dec. 12, 1997

[51] Int. Cl.$^6$ .................................................. C12Q 1/70
[52] U.S. Cl. ........................ 435/5; 435/7.1; 435/7.72; 424/204.1; 424/231.1
[58] Field of Search .......................... 435/5, 7.1, 7.72, 435/7.9, 7.94; 530/350; 424/204.1, 231.1

[56] References Cited

U.S. PATENT DOCUMENTS

| | | |
|---|---|---|
| 4,430,347 | 2/1984 | Oiry et al. . |
| 4,764,459 | 8/1988 | Hampar et al. . |
| 4,855,224 | 8/1989 | Berman et al. . |
| 5,149,660 | 9/1992 | Cohen et al. . |

OTHER PUBLICATIONS

Jian–Hua Luo, Cynthia C. Smith, Michael Kulka, Laure A Truncated Protein Kinase Domain of the Large Subunit of Herpes Simplex Virus Type 2 Ribonucleotide Reductase (ICP10) Expressed in *Escherichia coli*, Journal of Biological Chemistry, 1991, pp. 20976–20983, vol. 266.

L.Aurelian, P.Terzano, C.C.Smith, T.Chung, A.Shamsuddin Amino–terminal Epitope of Herpes Simplex Virus Type 2 ICP10 Protein as a Molecular Diagnostic Marker for Cervical Intraepithelial Neoplasia, Cancer Cells 7, 1989, pp. 187–191, Cold Spring Harbor Laboratory.

Tao Peng, James R.C.Hunter, John W.Nelson The Novel Protein Kinase of the RR1 Subunit of Herpes Simplex Virus Has Autophosphorylation and Transphosphorylation Activity That Differs in Its ATP Requirements for HSV–1 and HSV–2, Infection and Immunity, Apr. 1983.

J.M.Middeldorp, A.M.Hooymans, A.J.H.F.Kocken, A.M.Van A sensitive enzyme–linked immunosorbent assay for the detection of herpes simplex virus antigens, Journal of Virological Methods, 1987, pp. 159–174, vol. 17, Elsevier Science Publishers B.V.

David I. Bernstein, Francis K.Lee, Gary Echler, Andre Clinical and Serological Outcome of Genital Herpes Simplex Virus (HSV) Type 2 Inoculation following Oral HSV Type 1 Infection in Guinea–pigs, Journal of General Virology, 1989, pp. 2365–2372, vol. 70.

David Siegel, Eve Golden, A.Eugene Washington, Stephen Prevalence and Correlates of Herpes Simplex Infections The Population–Based AIDS in Multiethnic Neighborhoods Study, Journal of the American Medical Association, 1992, pp. 1702–1708, vol. 268, No. 13.

Homayon Ghiasi, Ravi Kaiwar, Anthony B. Nesburn, Susan Expression of Seven Herpes Simplex Virus Type 1 Glycoproteins (gB, gC, gD, gE, gG, gH, and gI): Comparative Protection against Lethal Challenge in Mice, Journal of Virology, 1994, pp. 2118–2126, vol. 68, No. 4.

Ann M.Arvin, Celine M.Koropchak, Anne S.Yeager, Lenore Pereira Detection of Type–Specific Antibody to Herpes Simplex Virus Type 1 by Radioimmunoassay with Herpes Simplex Virus Type 1 Glycoprotein C Purified with Monoclonal Antibody, Infection and Immunity, 1983, pp. 184–189, vol. 40, No. 1.

Peter R. Field, David W.T. Ho, William L. Irving, Davi The reliability of serological tests for the diagnosis Pathology, 25, 175–179, 1993.

Sharon Safrin, Ann Arvin, John Mills, Rhoda Ashley Comparison of the western immunoblot assay and a glyco Journal Clinical Microbiology, 30, 1312–1314, 1992.

Ioannis Nikas, John McLauchlan, Andrew J. Davison, Wil Proteins, structure, function and genetics. 1,376–384 1986. Structural features of ribonucleotide reductase.

*Primary Examiner*—Mary E. Mosher
*Assistant Examiner*—Ali R. Salimi
*Attorney, Agent, or Firm*—William S. Ramsey; Pepper Hamilton LLP

[57] ABSTRACT

The present method relates to the serological detection of herpes simplex virus type 2 (HSV-2) infection by means of reaction of a patient serum with a peptide specific to HSV-2 having the sequence Ala-Arg-Ser-Pro-Glu -Arg-Gln-Glu-Pro-Arg-Glu-Pro-Glu. The peptide may be further modified by the addition of a Cys or a biotin molecule. The peptide may be used in any of a number of assays including enzyme linked immunosorbent assay (ELISA), a radioimmunoassay (RIA), and other forms of immunoassay such as enzyme immunoblotting assay on a suitable adsorbent paper or an agglutination assay using the peptide composition as the antigen.

10 Claims, 10 Drawing Sheets

SEROLOGICAL ASSAY FOR HERPES

FIELD OF THE INVENTION

The present invention is a method for determining whether an individual has an infection of herpes simplex type 2 (HSV-2) by using a peptide which is immunoreactive with HSV-2 antibody present in infected individuals.

DESCRIPTION OF THE RELATED ART

A number of patents for the determination of HSV-2 as opposed to HSV-1 infection have issued. U.S. Pat. No. 4,430,347 discloses monoclonal antibodies in a diagnostic kit for differentiating HSV-1 and HSV-2. U.S. Pat. No. 4,855,224 discloses the use of glycoprotein D of HSV-1 and glycoprotein C from HSV-2 for differentiating the two types. U.S. Pat. No. 5,149,660 discloses envelope glycoproteins gD-1 and gD-2 as useful for differentiating HSV1 and 2. U.S. Pat. No. 4,764,459 discloses the use of immunoaffinity purified virus-coded glycoproteins as target antigens.

The tests now available for determining whether an infection is caused by HSV-1 or HSV-2 are quite variable in their effectiveness. Safrin et al (*Comparison of the Western Immunoblot Assay and a glycoprotein G Enzyme Immunoassay for Detection of Serum Antibodies to Herpes Simplex Virus Type 2 in Patients with AIDS*, Journal of Clinical Microbiology, Vol 30, pp. 1312–4, 1992) found that 77% of patients with AIDS were positive for HSV-2 by a Western blot against glycoprotein G-2 while only 48% were positive on immunoassay against the same protein. Field et al (*The Reliability of Serological Tests for the Diagnosis of Genital Herpes: A Critique*, Pathology, Vol 25, pp. 175–179, 1993) found the reliability of tests based on complement fixation were at best 87% accurate and after 28 days post-infection they were 0–57% accurate.

SUMMARY OF THE INVENTION

One object of the present invention is to provide a method for distinguishing infection in a subject with HSV-1 or HSV-2 using a serological assay. Another object of the invention is to provide an assay which is able to distinguish HSV-1 antibodies from HSV-2 antibodies. Yet another aspect of the invention is to diagnose a patient suspected of having been infected with HSV-2.

Au-1 peptide has the structure Ala-Arg-Ser-Pro-Ser-Glu-Arg-Gln-Glu-Pro-Arg-Glu-Pro-Glu (SEQ ID NO: 1). This peptide was initially determined to be antigenic when conjugated with keyhole limpet hemocyanin (KLH), a known promoter of antigenicity. The solid phase synthesis of the Au-1 peptide, its conjugation to KLH via an additional Cys residue and polyclonal antibody production in rabbits has also been described as well as this antibody's reactivity with HSV-2 infected cells and cancer cells (Aurelian et al., Cancer Cells, Vol. 7, pp. 187–191, 1989). Antibody to the peptide was used as a molecular diagnostic marker for cervical intraepithelial neoplasia. However, the peptide was not suspected to be of sufficient size or specificity to function in a serological diagnosis for HSV-2. Au-1 was known to be located in a domain encoded by transforming DNA sequences which had a (38%) homology with its HSV-1 counterpart (Nikas et al, Proteins Structural Function Genetics, Vol. 1, pp. 376, 1986). A further question was whether this peptide represents a site on HSV-2 that was sufficiently antigenic to generate antibodies by all persons infected with HSV-2. Interestingly we have found that the peptide, which consists of only 14 amino acids, is specific for HSV-2 and that antibody produced by persons infected with HSV-2 reacts specifically with the peptide which does not cross-react with antibodies to HSV-1, thus providing an excellent tool for the serological diagnosis of HSV-2 infection.

DETAILED DESCRIPTION OF THE EMBODIMENTS

The present invention provides a unique assay system which is able to distinguish an HSV-1 infection from an HSV-2 infection. A series of peptides have been previously synthesized and found to be highly immunogenic in rabbits when coupled to KLH. These peptides have been found to provide antibodies that react with HSV. These peptides consist of amino acids 13 to 26 from a sequence of HSV-2 designated as the PK domain in a protein designated ICP10. Although it was known that antibody to this sequence would react with HSV-2, it was not known whether the degree of specificity for HSV-2 was sufficient to distinguish HSV-2 from HSV-1. Further, it was not known that this sequence would be reactive when immobilized on a solid support. As a means for giving further latitude in the ability of the peptide to cross react, a Cys residue was added to provide flexibility to the peptide junction with the site of adsorption or reaction with the solid surface. To provide even further latitude, a biotin was added. Surprisingly, the sequence worked with or without the biotin.

This reactivity of the peptide when immobilized on a support afforded a method of detecting HSV-2 antibodies in a sample by contacting a patient serum with the peptide, which then react to form an antibody-antigen complex, and examining the resulting complex for reaction by a method of quantitation. A number of methods of examination of the quantity and/or presence of the antibody-antigen complex are suitable for this purpose. A Western blot assay may be performed by attaching the antigen to a nitrocellulose paper and staining with an antibody which has a dye attached. Among the methods using a reporter enzyme is the use of a reporter-labeled antihuman antibody. The label may be an enzyme, thus providing an enzyme-linked immunosorbent assay (ELISA). It may be a radioactive element, thus providing a radioimmunoassay (RIA).

With the method of examining a patient serum for the quantity/presence of HSV-2 antibody, a diagnostic assay kit containing the assay and controls for positive and/or negative reactions, with or without washing buffers and other necessary ingredients may be assembled.

These and other objects of the invention will become apparent by a careful consideration of the examples and the accompanying figures.

EXAMPLE 1
Reactivity of Covalently Bound Au-1 Peptide

Figure 1:
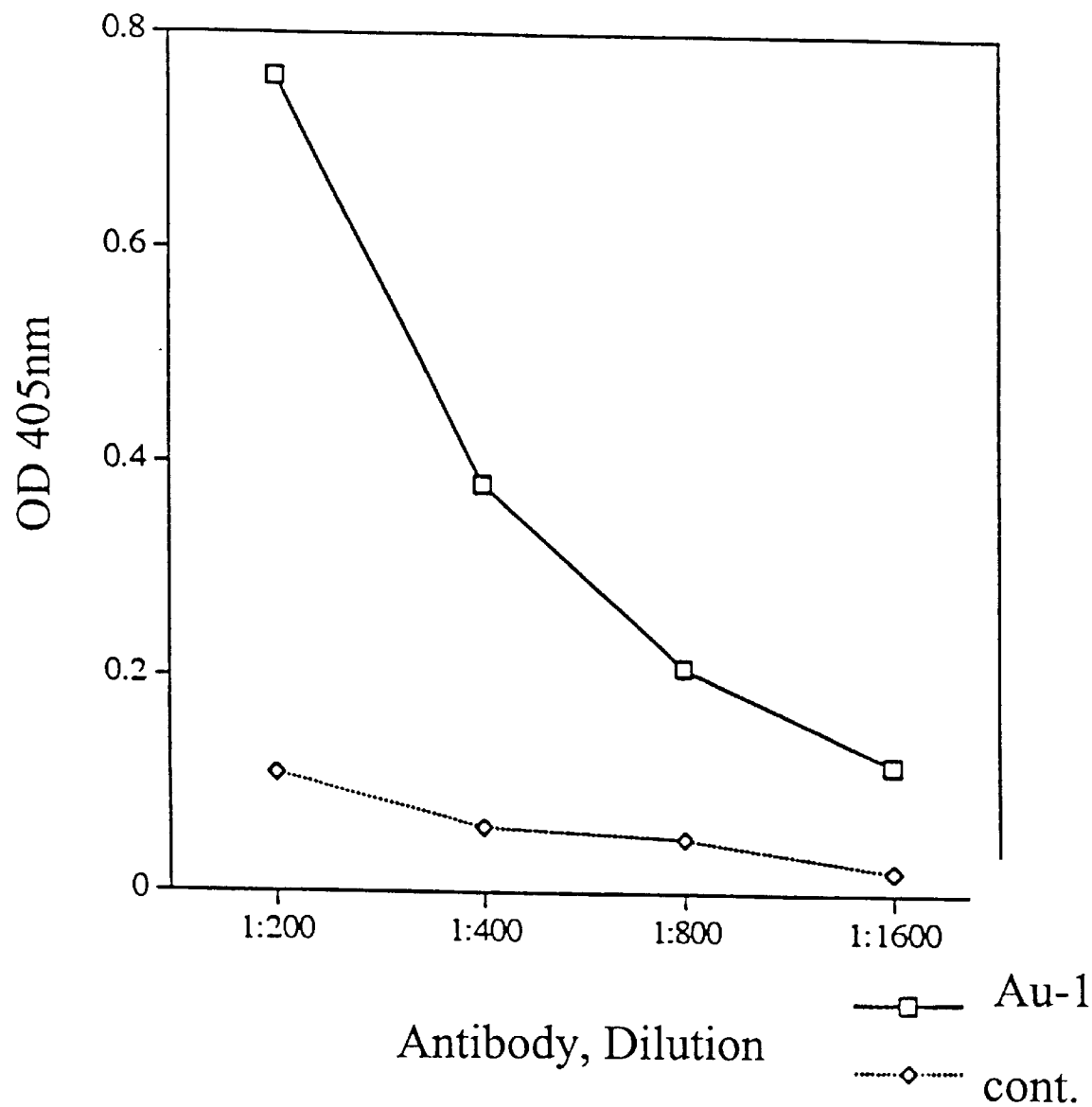
FIG. 1 is a graph of the reaction of dilutions of anti-Au-1 IgG with a constant amount of covalently bound Au-1.

The Au-1 peptide, Ala-Arg-Ser-Pro-Ser-Glu-Arg-Gln-Glu-Pro-Arg-Glu-Pro-Glu (SEQ ID NO: 1), was synthesized and conjugated to biotin at the amino terminus. It was purified by HPLC and the sequence was verified by microsequencing. In a first series of experiments, the peptide (5 μg/mL) was covalently attached (100 μl/well) to Xenobind plates (Xenopore Corp. Hawthorne, N.J.) in 0.1M sodium bicarbonate (pH 9.2) by incubation at 25° C. for 16 hours. The plates were blocked by incubation (1 hr, 37° C.) with 1% bovine serum albumin (BSA) in phosphate buffered saline (1% BSA-PBS) and washed 3 times with PBS-0.05% Tween 20. Selected wells were blocked without peptide and used as control. It was assayed with the IgG fraction isolated from the anti-Au-1 serum using protein A. Serial dilutions of anti-Au-1 IgG beginning at 1:200 were made in 1% BSA-PBS and 100 μl added to the plates for 30 minutes. The plates were washed 3 times with PBS-0.05% Tween 20. Horseradish peroxidase conjugated protein A (1:5000 dilution in 1% BSA-PBS) was added to the wells (100 μl) and incubated for 20 minutes. The plates were washed 3 times and 100 μl of ABTS substrate (KPL Labs, Gaithersburg, Md.) was added. Following incubation for 10 min the plates were read at 405 nm with a Biotek EL800 microplate reader, blanked on air. The anti-Au-1 IgG gave a strong reaction with the Au-1 peptide (FIG. 1). The reactivity was specific and was not observed in the absence of peptide (FIG. 1). Antibody titer, expressed as the reciprocal of the highest dilution that gave rise to a reactivity 2-fold higher than the maximal response seen in the absence of peptide was 1600. This shows that anti-Au-1 IgG gave a strong specific reaction with covalently bound Au-1 peptide.

EXAMPLE 2
Reactivity of Passively Bound Au-1 Peptide

Figure 2:
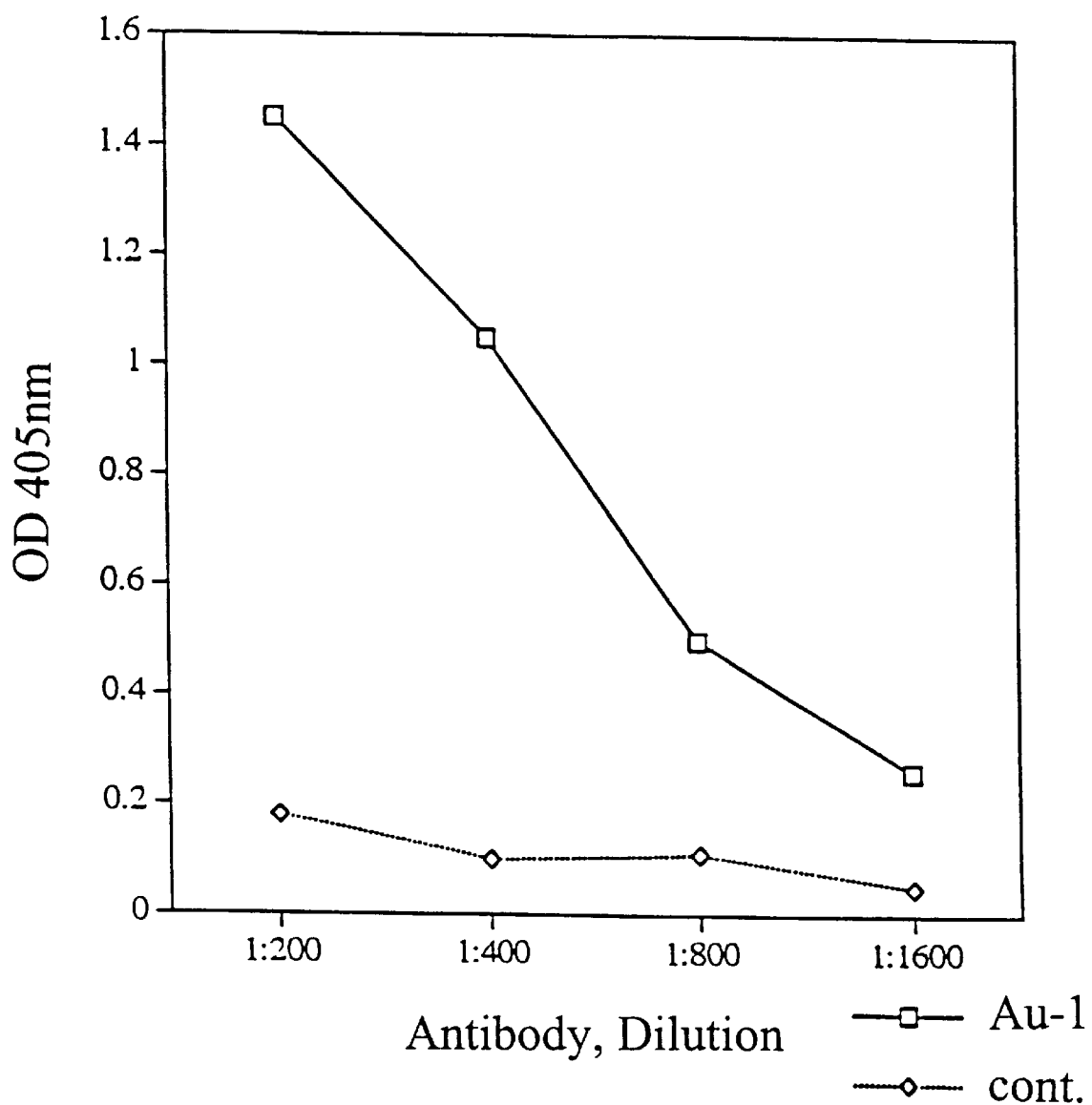
FIG. 2 is a graph of the reaction of Au-1 peptide which was passively adsorbed to the plates with dilutions of anti-Au-1 antibody.

The Au-1 peptide (5 μg/ml) in 0.1M sodium bicarbonate (pH 9.2) was allowed to passively bind (100 μl/well) to 96 well plates for 16 hrs at room temperature. The unbound peptide was removed and the plates were blocked with 1% BSA-PBS for 10 minutes. Selected wells were blocked without peptide and used as control. As shown in FIG. 2, the Au-1 peptide which was passively adsorbed to the plates reacted with the Au-1 antibody. The antibody titer, defined as described in Example 1, was 1600. This shows that the Au-1 peptide which was passively absorbed reacted with the Au-1 antibody with a titer of 1600.

EXAMPLE 3
Reactivity of Human Sera with Covalently Bound Au-1 Peptide

Figure 3:
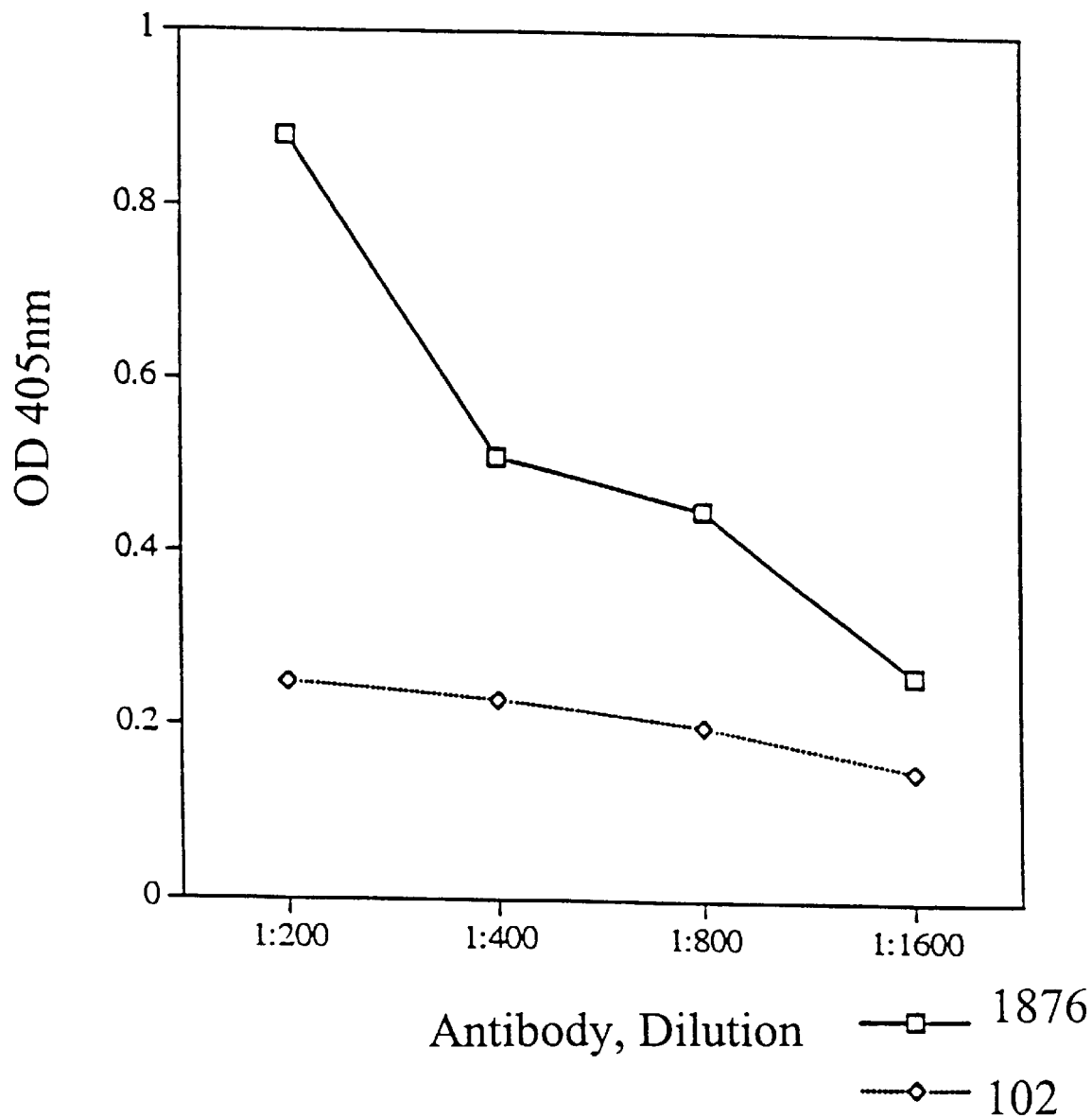
FIG. 3 shows the reactivity of various dilutions of sera from patients with known HSV-1 or HSV-2 infections with Au-1 peptide covalently bound to a microtiter plate.

Sera were selected from patients with herpes virus infection confirmed by virus isolation and typed as HSV-2 (#105, #106, #1827, and #1876) or HSV-1 (#102, #103, #1837, #1838, and #1874) and were used in this and the following examples. Serum #1876, from a HSV-2 positive patient and serum #102, from a HSV-1 patient, were used for this experiment. The peptide (5 μg/ml) was covalently linked to the plates (Xenobind) in a 100 μl/well volume using 0.1M sodium bicarbonate (pH 9.2) by incubation at 25° C. for 16 hours. The plates were blocked by incubation (1 hr, 37° C.) with 1% BSA-PBS and washed 3 times with PBS-0.05% Tween 20. Selected wells were blocked without peptide as control. Sera were serially diluted beginning at 1:100 in 1% BSA-PBS and 100 μl/well were added to the plates. After incubation for 1 hr at 37° C., the plates were washed 3 times with PBS-0.05% Tween 20. Horseradish peroxidase labeled anti-human IgG (gamma-specific) was diluted 1:5000 in 1% BSA-PBS and added (100 μl/well) to the plates and incubated 30 minutes. The plates were washed 3 times and ABTS substrate (100 μl/well) was added and incubated 15 minutes. Plates were read at 405 nm as in Example 1. Absorbance values were normalized by subtraction of the signal from the wells without peptide antigen. As shown in FIG. 3, serum #1876 which was obtained from an HSV-2 patient, evidenced strong dose-dependent reactivity with the Au-1 peptide. By contrast, serum #102 which was obtained from an HSV-1 patient failed to show such reactivity, thus demonstrating that the Au-1 peptide reacts only with serum from HSV-2 patients.

EXAMPLE 4
Reaction of Au-1 Peptide with HSV-2 and HSV-1 Sera

Figure 4:
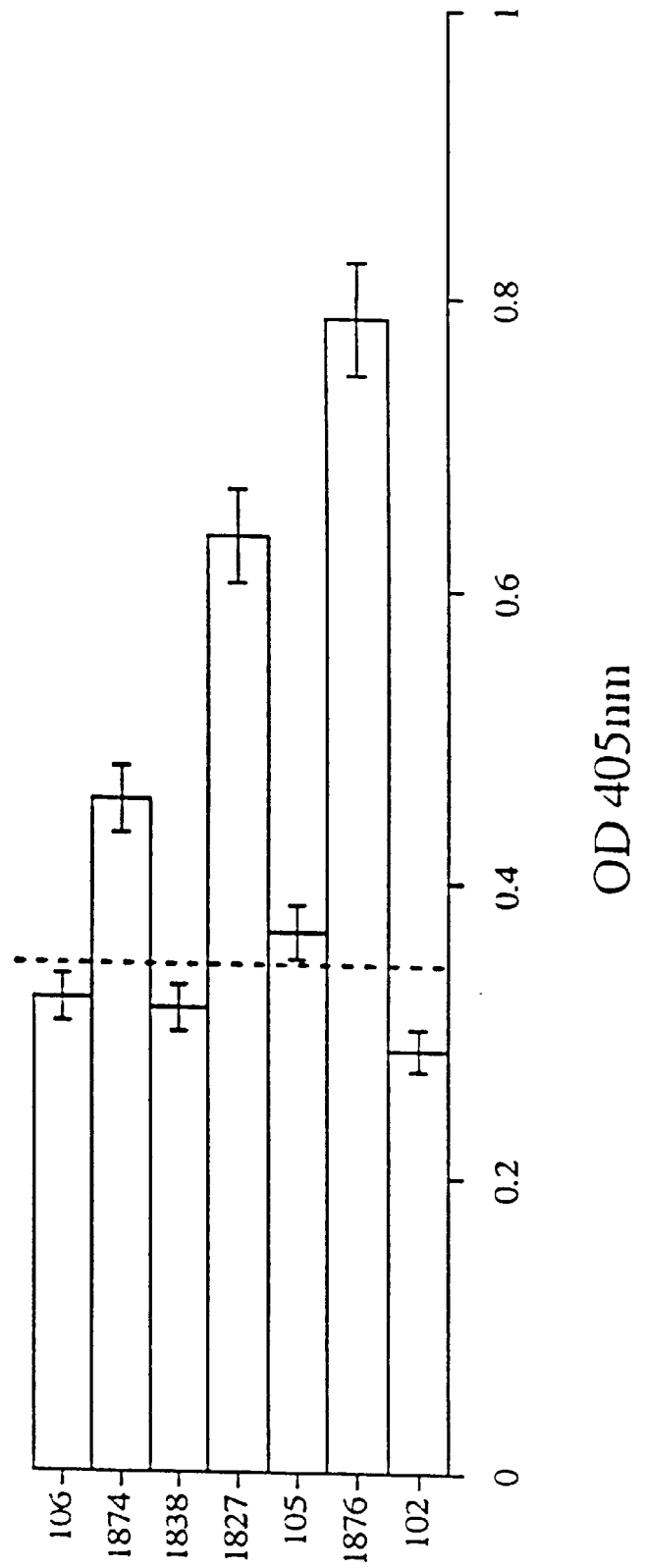
FIG. 4 shows the reproducibility of the reactivity of sera at various dilutions from patients with known HSV-1 or HSV-2 infections with Au-1 peptide covalently bound to a microtiter plate.

Sera were diluted 1:100 and assayed in triplicate on the peptide covalently bound to the plates as in Example 3. A cut-off point was established at OD=0.35 based on the reactivity of serum #102 in Example 3. All sera having OD values <0.35 were considered to be HSV-1 specific while those giving values >0.35 were considered to be HSV-2 specific. The assay is highly reproducible, with very tight standard deviation (SD) values, as shown in FIG. 4, a positive reaction was seen in 3 of 4 HSV-2 seras (75%) and 1/3 (33%) HSV-1 seras. The ability of the Au-1 peptide to specifically recognize other sera from HSV-2 patients was demonstrated.

EXAMPLE 5
Antibody Titration Using Au-1 Peptide Covalently Bound to Plate

Figure 5:
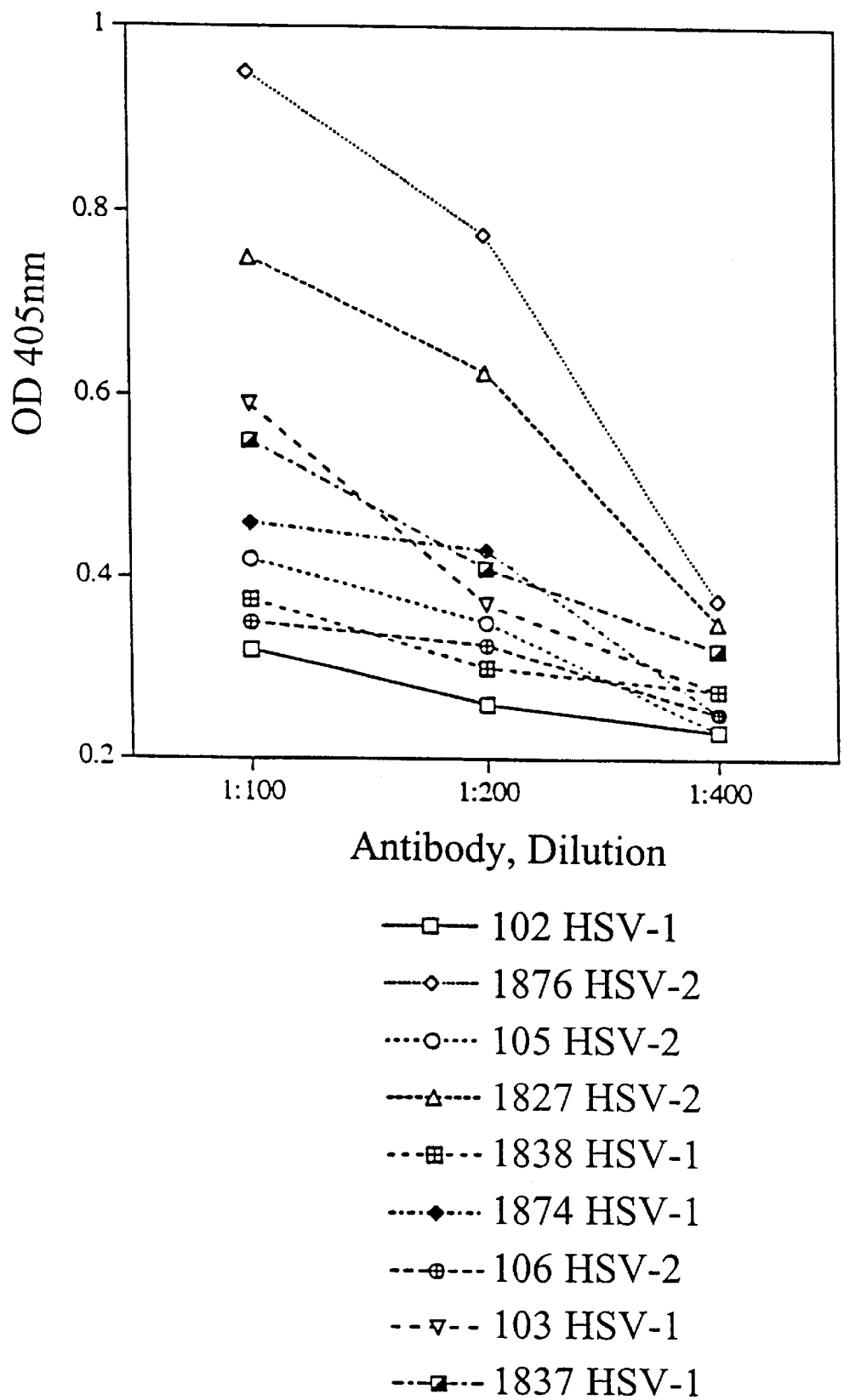
FIG. 5 shows the quantification of the reactivity of sera from patients with known HSV-1 or HSV-2 infections with Au-1 peptide covalently bound to a microtiter plate.

To obtain a quantitative estimate of the antibody levels in human sera, the assay was repeated using the covalently bound Au-1 peptide (Xenobind plates) and sera diluted from 1:100 to 1:400. The assay was carried out as described in Example 3, but with two different sets of controls. In the first series, the control was a reagent blank (no serum control). The mean OD value obtained from 10 such wells +2 standard deviations (SD) was subtracted from the ODs obtained for the sera and a cut-off point was established at 0.6 based on the reactivity of the HSV-1 sera which gave the highest OD values. All sera with ODs higher than 0.6 were considered HSV-2 positive while those with OD values lower than 0.6 were considered HSV-1 positive. The results are shown in FIG. 5. All HSV-1 sera failed to react with Au-1 peptide, yielding a 100% specificity level. By contrast, only 2/4 HSV-2 sera (#1876 and #1827) reacted with Au-1 peptide, yielding a 50% sensitivity level. The titers of the positive HSV-2 sera were 200.

Figure 6:
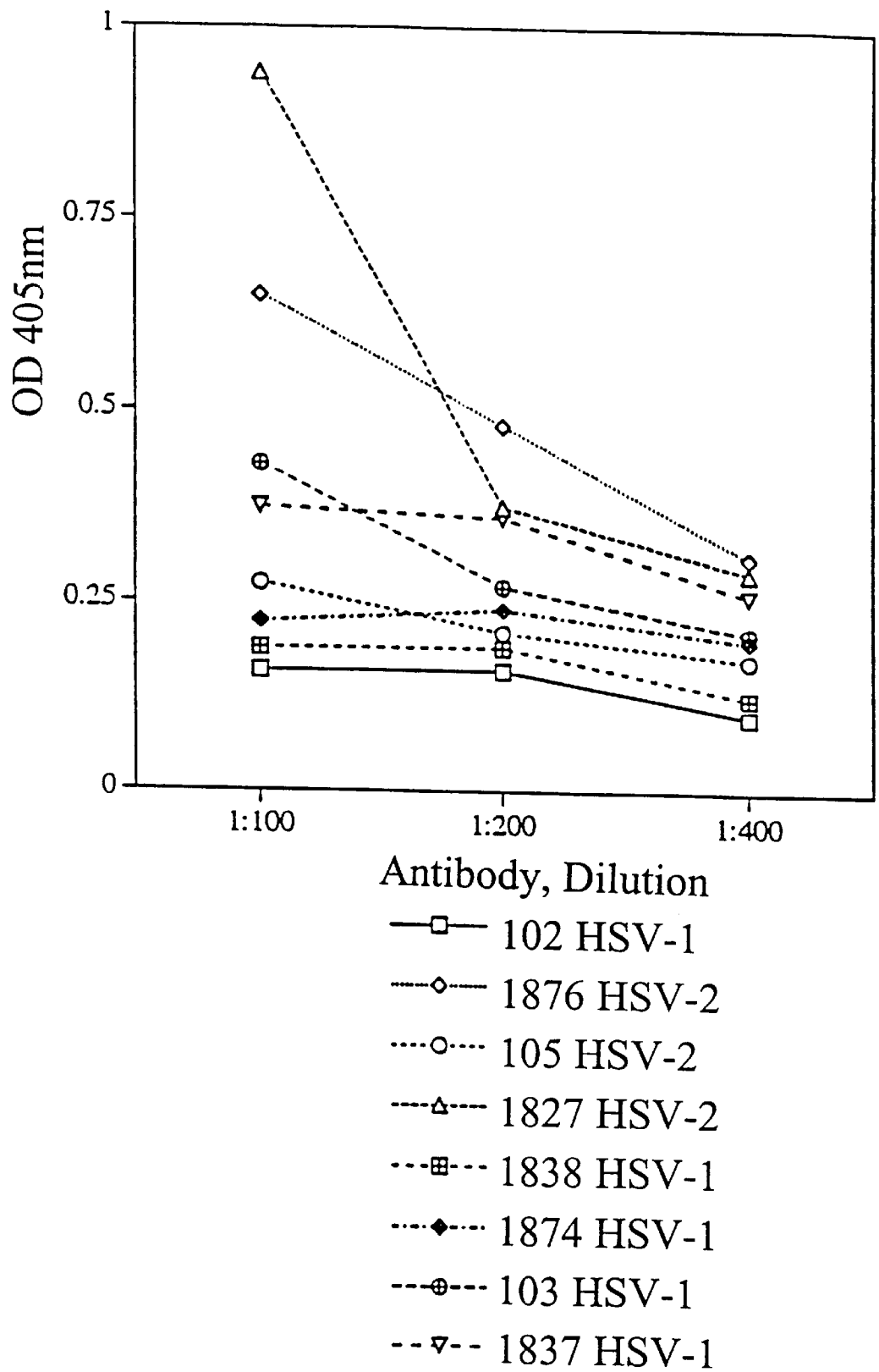
FIG. 6 shows the quantification of the reactivity of sera from patients with known HSV-1 or HSV-2 infections with Au-1 peptide covalently bound to a microtiter plate (control wells had no serum).

EXAMPLE 6
Antibody Titration with Covalently Bound Au-1 Peptide and no Peptide Control In this experiment, the assay was carried out as in Example 5, except that the control wells had no peptide placed in them. All sera were assayed in parallel on wells lacking peptide and the mean OD value +2SD was subtracted from the ODs obtained for the sera. A cut-off point was set up at 0.45 based on the reactivity of the HSV-1 sera. The results are shown in FIG. 6. Positive results were seen for HSV-2 sera #1876 and #1827, but not for another HSV-2 serum (#105) for a 75% sensitivity level. All HSV-1 sera were negative for a 100% specificity level. Thus, Au-1 peptide can be used for differentiation of HSV-2 vs HSV-1 antibody.

EXAMPLE 7
Reactivity of Human Sera with Passively Adsorbed Au-1 Peptide

Figure 7:
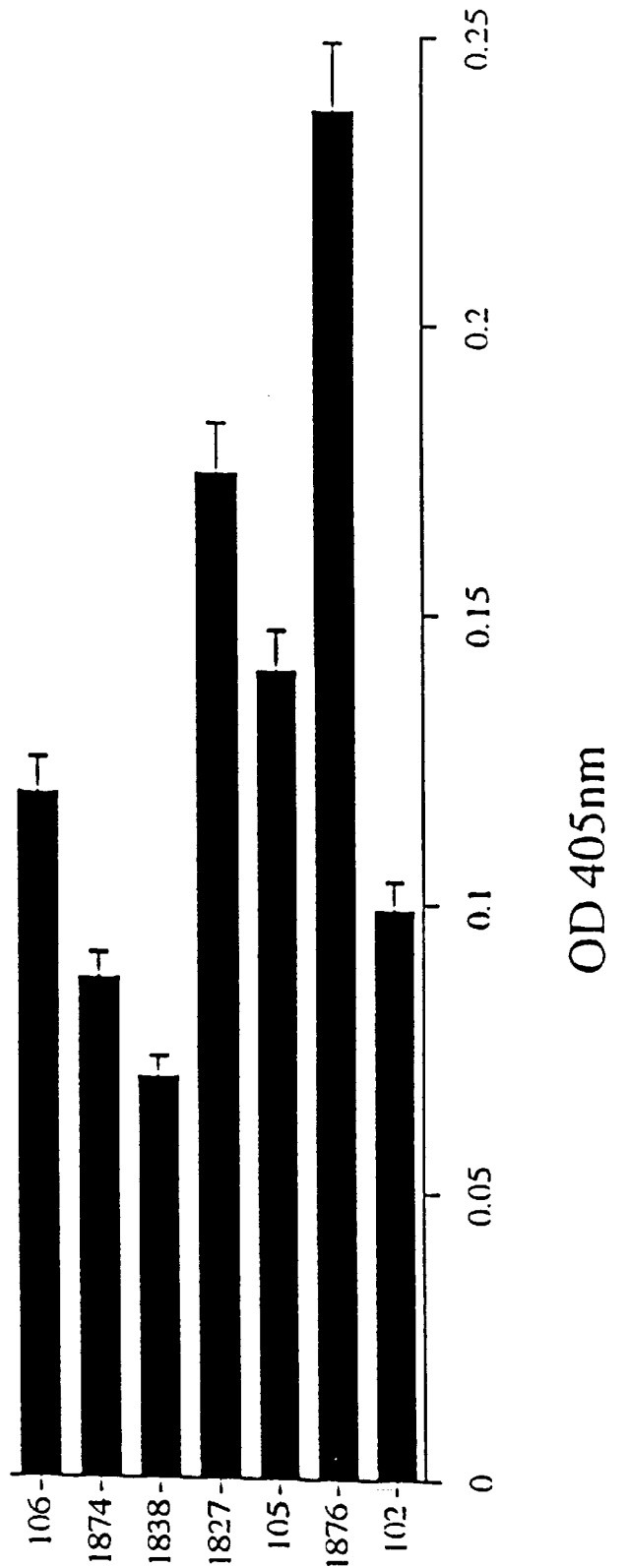
FIG. 7 shows the reactivity of sera from patients with known HSV-1 or HSV-2 infections (at various dilutions) with Au-1 peptide passively adsorbed to a microtiter plate.

In this experiment the sera from patients with HSV-2 or HSV-1 infections were assayed for their ability ro react with the Au-1 passively adsorbed to the plates. The Au-1 peptide (2.5–5 μg/mL) in 0.1M sodium bicarbonate (pH 9.2) was allowed to bind (100 μl/well) to 96 well plates which contain no covalent binding properties for 16 hrs at room temperature. The unbound peptide was removed and the plates were blocked with 1% BSA-PBS for 10 minutes. Selected wells were blocked without peptide as control. Sera were first diluted 1:100 in 1% BSA-PBS and 100 μl/well were added to the plates and incubated for 40 minutes. The plates were washed 4 times with PBS-0.05% Tween 20. Horseradish peroxidase conjugated anti-human IgG (gamma specific) (100 μl/well) diluted 1:10,000 in 1% BSA-PBS was added to the plates and incubated for 20 minutes. The plates were washed 3 times as above and ABTS substrate was added and incubated 15 min and plates were read at 405 nm as in Example 1. A cut-off point was set up at 0.1 based on the reactivity of the HSV-1 sera. As shown in FIG. 7, reproducibility is very good, with very tight SDs. All 4 HSV-2 sera are positive (including #105 and 106 that were negative on the Xenobind plates) while all the HSV-1 sera are still negative, for a 100% correlation level.

EXAMPLE 8
Antibody Titration with Passively Adsorbed Au-1 Peptide

Figure 8:
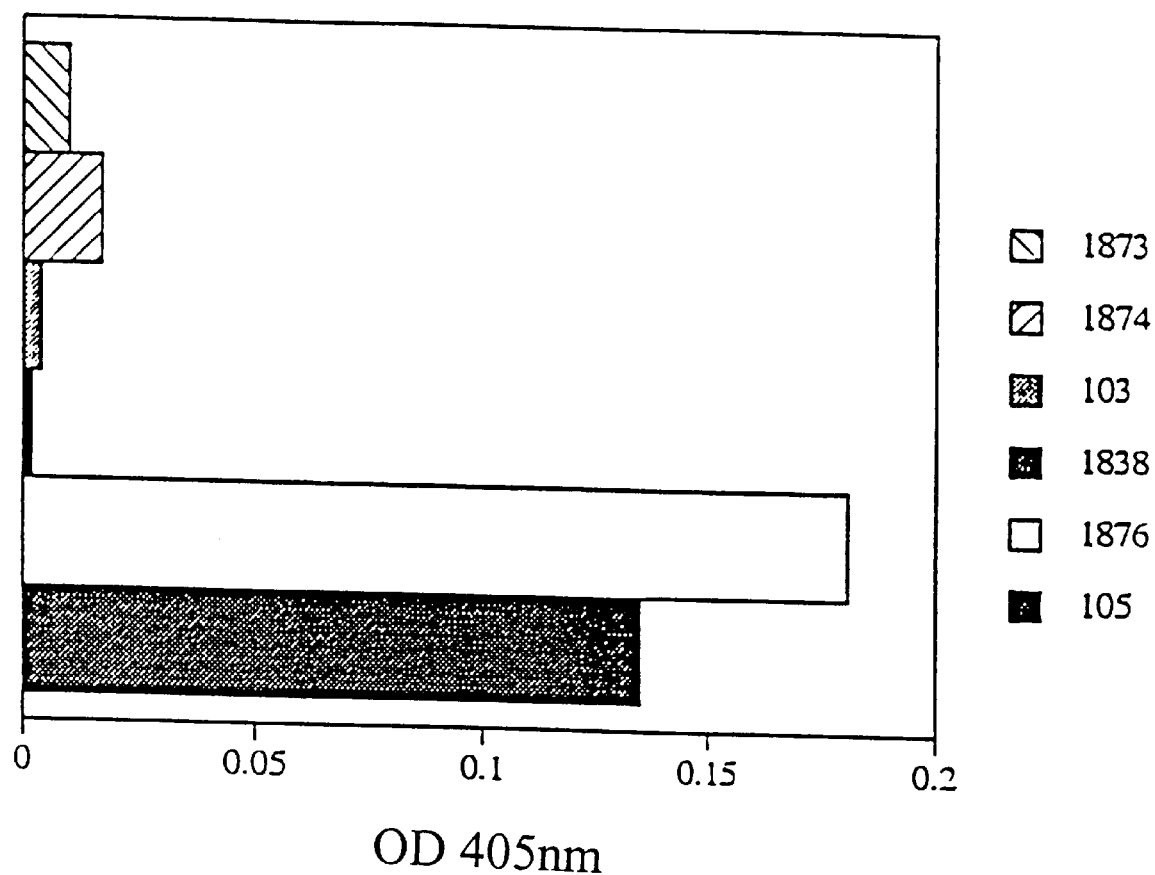
FIG. 8 shows quantification of the reactivity the of sera from patients with known HSV-1 or HSV-2 infections (at various dilutions) with Au-1 peptide passively absorbed to a microtiter plate (no peptide control).
Figure 9:
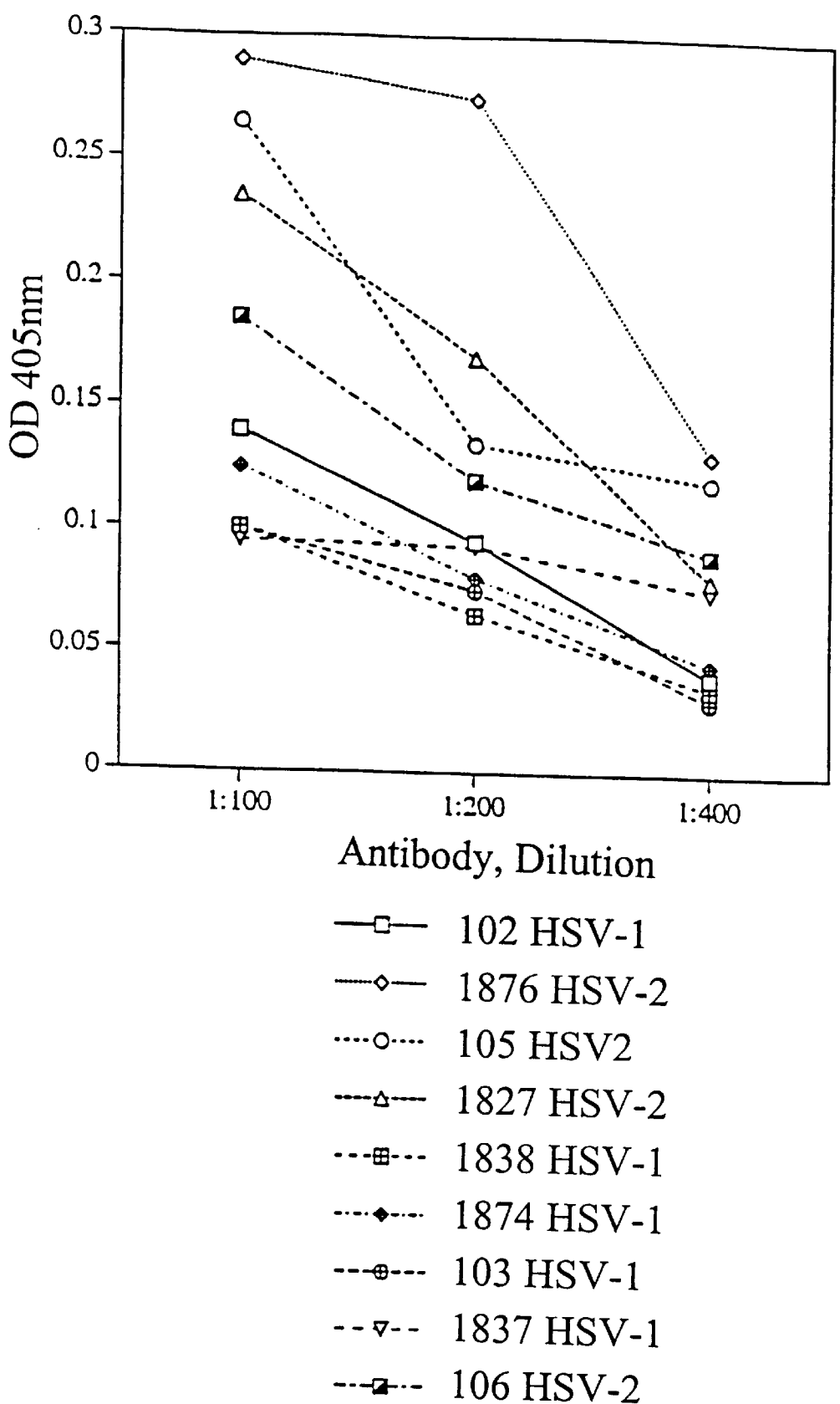
FIG. 9 shows the quantification of the reactivity of sera from patients with known HSV-1 or HSV-2 infections with Au-1 peptide passively absorbed to a microtiter plate (reagent blank control).

For quantitative estimation of the antibody titers sera were diluted 1:100–1:400 and assayed with passively adsorbed Au-1 peptide using the two different controls described in Examples 5 and 6, i.e., the reagent blank +2SD and the no peptide +2SD. As in Example 7, cut-off points were established based on the most reactive HSV-1 sera. The data in FIG. 8 were for a 1:200 dilution of the sera corrected for the no-peptide +2SD values. A 100% correlation with virus isolation is observed with positivity seen for #105 and #1876 (2/2 sera) while all 4 HSV-1 sera are negative. Analysis using the reagent blank control +2SD was graphed in FIG. 9 and it also shows a 100% correlation with the virus isolation data. Thus, 4/4 HSV-2 sera are positive as compared to 0/5 HSV-1 sera. Antibody titers are 2-fold lower for sera #105 and #106 (titer=100) than #1827 and #1876 (titer=200). The failure of these sera to react in the Xenobind assay may be due to this lower titer or to the masking of epitope(s) through covalent binding of the peptide.

These data indicate that the Au-1 peptide can be used to identify a HSV-2 positive serum and differentiate it from a HSV-1 serum. In this format (passive adsorbtion) there is 100% correlation with virus isolation, indicative of 100% levels of sensitivity and specificity.

EXAMPLE 9
Effect of Biotin Conjugation

Figure 10:
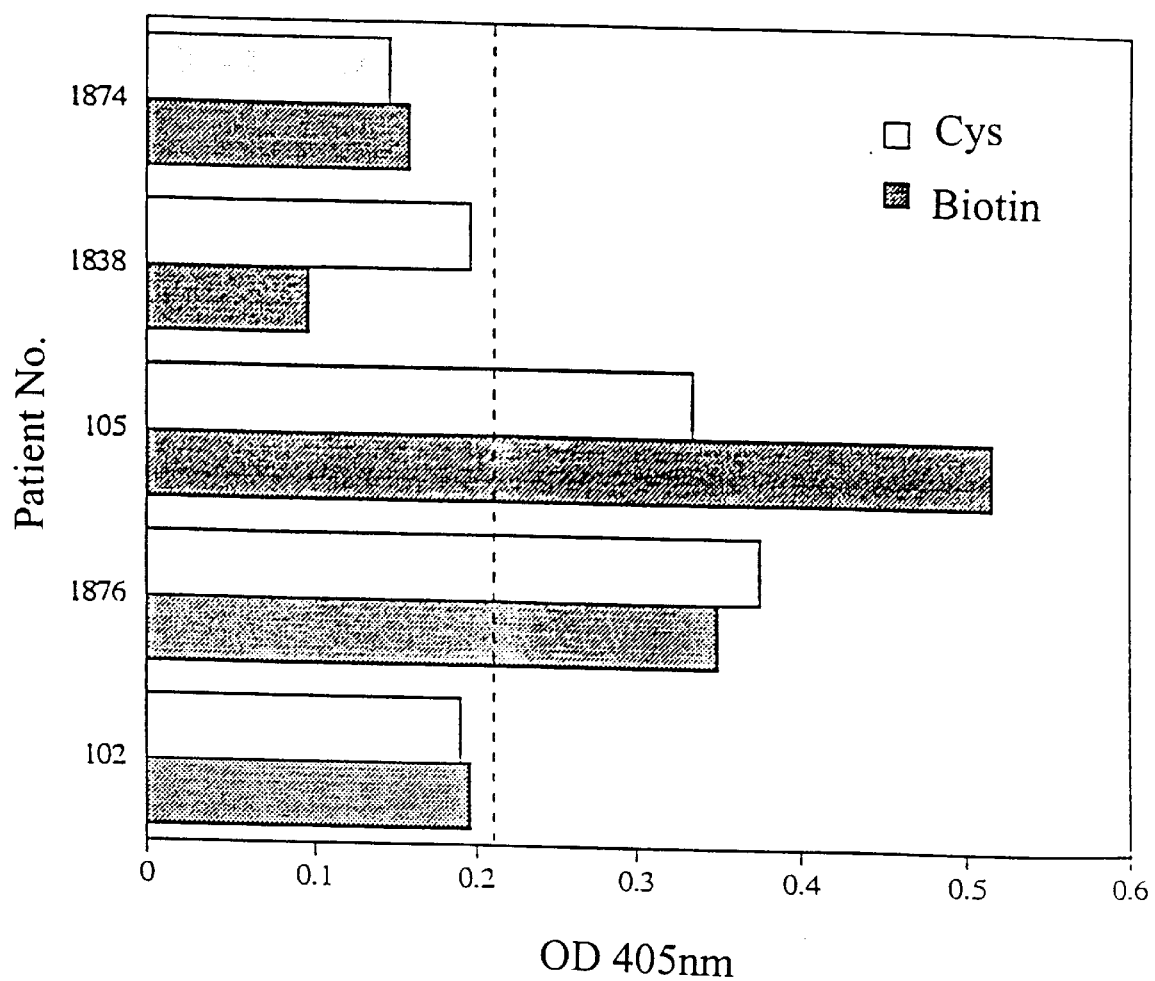
FIG. 10 shows the effect of a biotin extension of the peptide chain on the quantitative reactivity of sera from patients with known HSV-1 or HSV-2 infections (at various dilutions) with Au-1 peptide passively absorbed to a microtiter plate.

This experiment was designed to examine whether biotin conjugation of the Au-1 peptide is required in order to obtain the results described above. The passive adsorption format was used in these assays. The peptide was conjugated to biotin or unconjugated but with an additional N-terminal Cys residue. The assay was done with 5 μg/mL of either peptide and the sera were diluted 1:100. The control was the reagent blank (no serum) control +2SD. For most sera the corrected OD values obtained with the unconjugated Au-1 peptide were similar to those obtained with the biotin conjugated peptide (FIG. 10). The exceptions were serum #105 (HSV-2 patient) which gave a corrected OD of 0.516 with the biotin conjugated peptide as compared to 0.324 for the unconjugated peptide cys containing and serum #1838 (HSV-1 patient) which gave a corrected OD of 0.088 with the conjugated peptide as compared to 0.187 with the unconjugated peptide. Analysis based on a cut-off point determined by the reactivity of the HSV-1 sera (#102, #1838, #1874) for both the biotin conjugated and unconjugated peptides, indicates that a positive result was obtained for the HSV-2 sera (#105 and #1876) whether they are assayed with the biotin conjugated or unconjugated peptide (FIG. 10). These data support the conclusion that reactivity is due to the presence of antibody to Au-1 and suggest that conjugation with biotin, although not essential, did improve the differential recognition of the HSV-2 patient.

It will be apparent to those skilled in the art that the examples and embodiments described herein are by way of illustration and not of limitation, and that other examples may be utilized without departing from the spirit and scope of the present invention, as set forth in the appended claims.

---

We claim:

1. A method for detecting antibodies to HSV-2 in a serum sample without detecting antibodies to HSV-1 in such a sample comprising the steps:
   a. contacting the serum with a peptide having the structure of SEQ ID NO: 1, and
   b. examining the peptide for the presence of bound antibody.

2. The method of claim 1 wherein one or more cysteine has been added to the peptide.

3. The method of claim 1 wherein biotin has been added to the peptide.

4. The method of claim 1 wherein one or more cysteine and biotin have been added to the peptide.

5. The method of claim 1 wherein the peptide is attached to a support.

6. The method of claim 1 wherein the step of examining the peptide for the presence of bound antibody includes the use of a reporter-labeled anti-human antibody.

7. The method of claim 1 wherein the step of examining the peptide for the presence of bound antibody includes the use of an enzyme-linked immunosorbent assay.

8. The method of claim 1 wherein the step of examining the peptide for the presence of bound antibody includes the use of a Western Blot assay.

9. The method of claim 1 wherein the step of examining the peptide for the presence of bound antibody includes the use of a radio immunoassay.

10. The method of claim 1 further comprising the step:
    c. and quantifying the amount of antibody bound to the peptide.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 14

```
          (B) TYPE: AMINO ACID
          (C) STRANDEDNESS:
          (D) TOPOLOGY: LINEAR (ii) MOLECULE TYPE: PEPTIDE (iii) HYPOTHETICAL: NO (iv) ANTI-SENSE:    NO (v) FRAGMENT TYPE: INTERNAL (vi) ORIGINAL SOURCE:
          (A) ORGANISM: HERPES SIMPLEX
          (B) STRAIN:   WILD TYPE
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:  Swain, M. A.
              Galloway, D.A.
          (B) TITLE:    Herpes Simplex Virus Specifies Two Subunits of
                        Ribonucleotide
              Reductase Encoded by 3'-Coterminal Transcripts
          (C) JOURNAL:  Journal of Virology
          (D) VOLUME:   57
          (E) ISSUE:    3
          (F) PAGES:    802-8028
          (G) DATE:     1986
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:1:

Ala Arg Ser Pro Ser Glu Arg Gln Glu Pro Arg Glu Pro Glu
  1               5                   10
```